US012076479B2

(12) United States Patent
Koltz, Jr.

(10) Patent No.: US 12,076,479 B2
(45) Date of Patent: Sep. 3, 2024

(54) LOW PRESSURE INSUFFLATION MANIFOLD ASSEMBLY FOR SURGICAL GAS DELIVERY SYSTEM

(71) Applicant: Conmed Corporation, Utica, NY (US)

(72) Inventor: Michael Koltz, Jr., Aurora, CO (US)

(73) Assignee: Conmed Corporation, Largo, FL (US)

( * ) Notice: Subject to any disclaimer, the term of this patent is extended or adjusted under 35 U.S.C. 154(b) by 334 days.

(21) Appl. No.: 17/376,561

(22) Filed: Jul. 15, 2021

(65) Prior Publication Data

US 2022/0233795 A1 Jul. 28, 2022

Related U.S. Application Data

(63) Continuation-in-part of application No. 17/155,478, filed on Jan. 22, 2021, and a continuation-in-part of application No. 17/155,572, filed on Jan. 22, 2021.

(51) Int. Cl.
*A61M 13/00* (2006.01)
*A61B 17/34* (2006.01)

(52) U.S. Cl.
CPC ........ *A61M 13/006* (2014.02); *A61M 13/003* (2013.01); *A61B 17/3474* (2013.01); *A61B 17/3498* (2013.01); *A61B 2562/0247* (2013.01)

(58) Field of Classification Search
CPC .. A61M 13/006; A61M 13/00; A61M 13/003; A61M 2205/3344; A61M 2205/3331; A61M 2205/3341; A61M 2205/3337; A61M 5/16813; A61M 5/16881; A61M 5/172; A61M 39/22;

(Continued)

(56) References Cited

U.S. PATENT DOCUMENTS 7,325,780 B2 2/2008 Arai et al.
7,854,724 B2 12/2010 Stearns et al.
(Continued)

FOREIGN PATENT DOCUMENTS

JP 2016052478 A 4/2016

OTHER PUBLICATIONS

PCT International Search Report dated May 11, 2022, issued during the prosecution of PCT/US2022/013063.

(Continued)

*Primary Examiner* — Kami A Bosworth
*Assistant Examiner* — Avery Smale
(74) *Attorney, Agent, or Firm* — Locke Lord LLP; Scott D. Wofsy (57) ABSTRACT

A manifold assembly for a surgical gas delivery system is disclosed, which includes a manifold body having an inlet port for receiving insufflation gas from a gas source by way of a high pressure regulator, a first outlet port for delivering the insufflation gas to a first access port and a second outlet port for delivering the insufflation gas to a second access port, a first outlet line valve operatively associated with the first outlet port, wherein the first outlet line valve includes a first electro-mechanical valve actuator for dynamically controlling a flow of the insufflation gas to the first access port, and a second outlet line valve operatively associated with the second outlet port, wherein the second outlet line valve includes a second electro-mechanical valve actuator for dynamically controlling a flow of the insufflation gas to the second access port.

20 Claims, 8 Drawing Sheets (58) Field of Classification Search
CPC ........ A61M 2205/128; A61M 2205/12; A61M 2205/121; A61B 17/3474; A61B 17/3498; A61B 2562/0247; A61B 17/3423; A61B 17/3462; A61B 2217/005
See application file for complete search history.

(56) References Cited

U.S. PATENT DOCUMENTS

| | | | |
|---|---|---|---|
| 8,795,223 | B2 | 8/2014 | Stearns et al. |
| 9,199,047 | B2 | 12/2015 | Stearns et al. |
| 9,375,539 | B2 | 6/2016 | Stearns et al. |
| 10,384,021 | B2 | 8/2019 | Koeth et al. |
| 10,557,562 | B2 | 2/2020 | Sattelberg et al. |
| 10,702,306 | B2 | 7/2020 | Silver et al. |
| 2009/0012448 | A1* | 1/2009 | Childers ............. A61M 1/1561 604/29 |
| 2014/0309583 | A1 | 10/2014 | Stearns et al. |
| 2015/0202389 | A1* | 7/2015 | Stearns ............. B01D 46/0008 604/23 |
| 2018/0214631 | A1* | 8/2018 | Amirouche ........... A61M 5/142 |
| 2018/0236186 | A1 | 8/2018 | Stearns et al. |
| 2020/0187667 | A1 | 6/2020 | Shakal |

OTHER PUBLICATIONS

PCT Written Opinion dated May 11, 2022, issued during the proseution of PCT/US2022/013063.

* cited by examiner

LOW PRESSURE INSUFFLATION MANIFOLD ASSEMBLY FOR SURGICAL GAS DELIVERY SYSTEM

CROSS-REFERENCE TO RELATED APPLICATIONS

The subject application is a continuation-in-part of U.S. application Ser. No. 17/155,478 filed Jan. 22, 2021, and a continuation-in-part of U.S. application Ser. No. 17/155,572 filed Jan. 22, 2021, the disclosures of which are both herein incorporated by reference in their entireties.

BACKGROUND OF THE INVENTION

1. Field of the Invention

The subject invention is directed to minimally invasive surgery, and more particularly, to a low pressure insufflation manifold assembly of a surgical gas delivery system used for gas sealed insufflation and gas recirculation during an endoscopic or laparoscopic surgical procedure.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the abdominal cavity, so that the surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. Nos. 7,854,724 and 8,795,223. These devices are constructed from several nested components including an inner tubular body portion and a coaxial outer tubular body portion. The inner tubular body portion defines a central lumen for introducing conventional laparoscopic or endoscopic surgical instruments to the surgical cavity of a patient and the outer tubular body portion defines an annular lumen surrounding the inner tubular body portion for delivering insufflation gas to the surgical cavity of the patient and for facilitating periodic sensing of abdominal pressure.

SurgiQuest has also developed multimodal surgical gas delivery systems for use with the unique gas sealed access devices described above. These gas delivery systems, which are disclosed for example in U.S. Pat. Nos. 9,199,047 and 9,375,539 have a first mode of operation for providing gas sealed access to a body cavity, a second mode of operation for performing smoke evacuation from the body cavity, and a third mode of operation for providing insufflation gas to the body cavity.

In the prior art SurgiQuest gas delivery system, the delivery or outflow of insufflation gas to the body cavity is controlled by solenoid valves, which have certain limitations with respect to the ability to control gas flow rates dynamically. For example, a solenoid valve with a 6 mm orifice has two flow states: zero and the 6 mm orifice flow as a function of the differential pressure. However, a 6 mm orifice proportional valve has an infinite number of intermediate flow settings, or equivalent orifice diameters.

Since flow is a function of the square of the orifice diameter, the additional intermediate valve positions of a proportional valve provide fine control beyond a simple linear relationship, as well as the ability to achieve stable flow rates at lower pressure, reduce pressure oscillation and eliminate pneumatic hammer. Furthermore, the first 10% of valve opening, or an effective orifice diameter of 0.6 mm, modulates one percent ($10\%^2$) of full-open flow; which could be favorable in pediatric applications.

SUMMARY OF THE DISCLOSURE

The subject application is directed to a new and useful low pressure manifold assembly for a multi-modal surgical gas delivery system, which is configured for facilitating insufflation during a laparoscopic surgical procedure. The low pressure manifold assembly includes a manifold body having an inlet port for receiving insufflation gas from a gas source by way of a high pressure regulator, a first outlet port for delivering insufflation gas to a first access port and a second outlet port for delivering insufflation gas to a second access port. In accordance with a preferred embodiment of the subject invention, the first access port is a valve sealed access port and the second access port in a gas sealed access port.

The manifold assembly further incudes a first outlet line valve operatively associated with the first outlet port of the manifold body, wherein the first outlet line valve includes an electro-mechanical valve actuator for dynamically controlling the flow of insufflation gas to the first access port, and a second outlet line valve operatively associated with the second outlet port of the manifold body, wherein the second outlet line valve includes an electro-mechanical valve actuator for dynamically controlling the flow of insufflation gas to the second access port.

The manifold body further includes an exhaust port for venting gas to atmosphere, wherein a ventilation exhaust valve is operatively associated with the exhaust port. The ventilation exhaust valve includes an electro-mechanical valve actuator for dynamically controlling the venting of gas from the exhaust port. The manifold body also includes a safety vent port for releasing gas to atmosphere, and a low pressure safety valve is operatively associated with the safety vent port. Preferably, the low pressure safety valve is a mechanical valve for controlling the release of gas from the safety vent port to limit a maximum intermediate pressure within the manifold assembly in the event of a power interruption, a pressure controller malfunction or if another valve sticks in an open position.

The manifold body also includes a primary proportional valve located upstream from the first and second outlet line valves. The primary proportional valve includes an electro-mechanical valve actuator for dynamically controlling the flow of insufflation gas to the first and second outlet line valves. The manifold body further includes a communication port for communicating with a pair of blocking valves that are located remote from the manifold assembly. A blocking valve pilot is operatively associated with the communication port, located upstream from the primary proportional valve. The blocking valve pilot includes an electro-mechanical valve actuator for dynamically controlling a flow of gas therethrough.

In one embodiment of the manifold assembly, each electro-mechanical valve actuator is configured as a motorized linear actuator, which includes a respective rack and pinion mechanism. Preferably, each rack and pinion mechanism includes a horizontal actuation shaft, a horizontal drive rack gear operatively associated with the horizontal actuation shaft, a rotatable drive pinion gear driven by the horizontal drive rack gear, and a vertical driven rack gear driven by the driven pinon gear and operatively associated with a spring-loaded vertical valve stem. Each horizontal drive rack gear is mounted to translate along a first horizontal axis, and each rotatable driven pinion gear is mounted to rotate about a second horizontal axis that extends perpendicular to the first horizontal axis.

In another embodiment of the manifold assembly, each electro-mechanical valve actuator is a motorized rotary actuator, which includes a reduction gear assembly operatively associated with a spring-loaded vertical valve stem. In yet another embodiment of the manifold assembly, each electro-mechanical valve actuator is a motorized rotary actuator, which includes an axial drive screw operatively associated with a spring-loaded vertical valve stem.

The manifold body also includes a first patient pressure sensor located downstream from the first outlet line valve and a second patient pressure sensor located downstream from the second outlet line valve for measuring abdominal pressure. In addition, the manifold body includes a first and second pressure sensors located upstream from the outlet line valves, which are associated with a venturi to measure a pressure differential used to infer a total gas flow rate from the manifold to the patient's body cavity. The manifold body also includes a pressure sensor downstream from the primary proportional valve and upstream from the outlet line valves.

These and other features of the manifold assembly of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas delivery system and method of the subject invention without undue experimentation, preferred embodiments thereof will be described in detail herein below with reference to the figures wherein:

FIGS. 12-14 are related views of an exemplary motorized rotary valve actuator shown in FIG. 11, which includes a stepper motor and an axial drive screw, wherein FIGS. 15-17 are related views of another motorized rotary valve actuator that includes a stepper motor and a reduction gear assembly, wherein

DETAILED DESCRIPTION OF THE PREFERRED EMBODIMENTS

Figure 1:
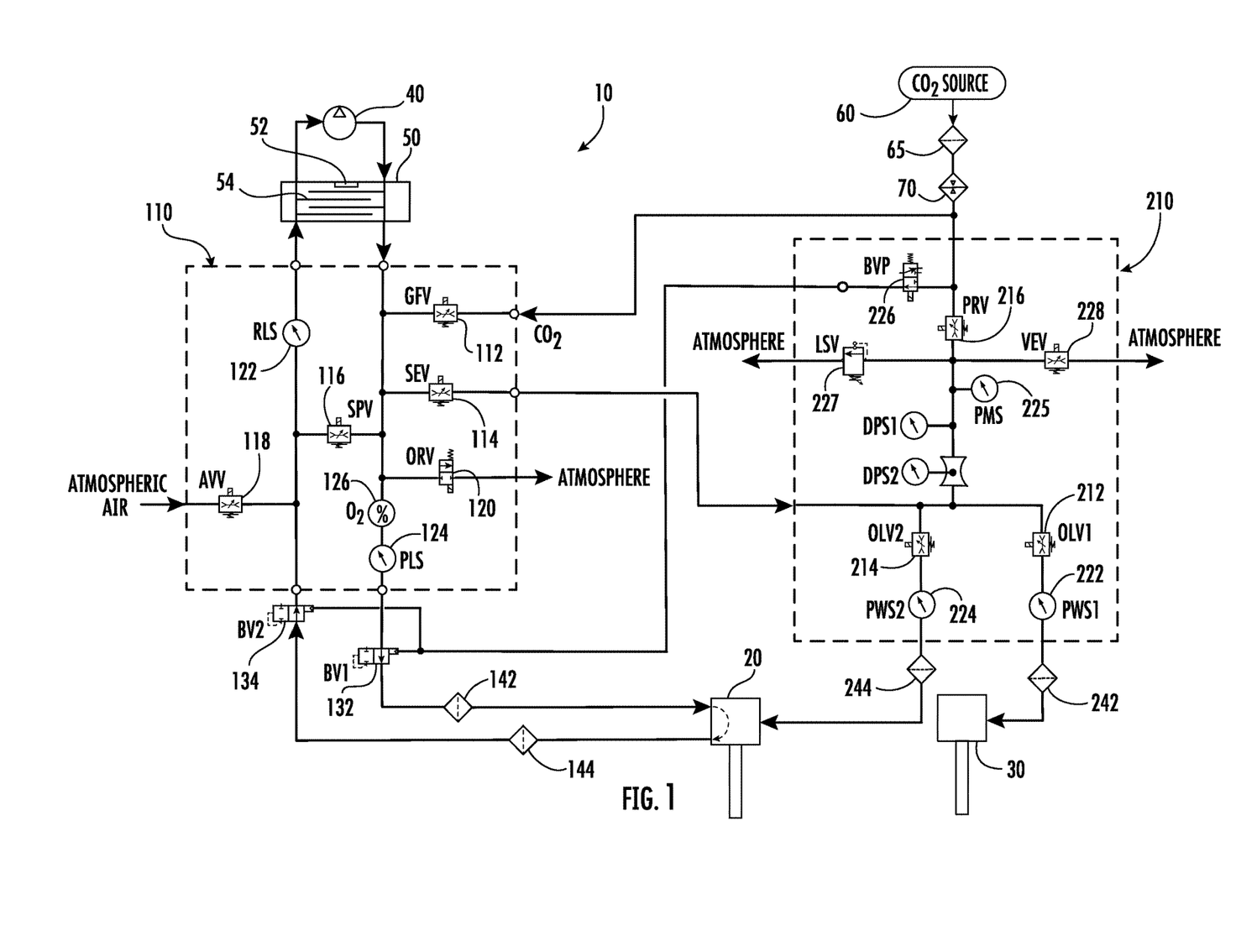
FIG. 1 is a schematic diagram of the multi-modal gas delivery system of the subject invention, which includes a gaseous sealing manifold for communicating with a gas sealed access port and a low pressure insufflation manifold for communicating with the gas sealed access port and with a valve sealed access port.

Referring now to the drawings wherein like reference numerals identify similar structural elements and features of the subject invention, there is illustrated in FIG. 1 a new and useful multi-modal surgical gas delivery system 10 that is adapted and configured for gas sealed insufflation, recirculation and smoke evacuation during an endoscopic or laparoscopic surgical procedure. The multi-modal surgical gas delivery system 10 of the subject invention includes a gaseous sealing manifold 110 for communicating with a gas sealed access port 20 and an insufflation manifold 210 for communicating with the gas sealed access port 20 and with a valve sealed access port 30.

The gas sealed access port 20 is of the type disclosed in commonly assigned U.S. Pat. No. 8,795,223, which is incorporated herein by reference. The gas sealed access port 20 is adapted and configured to provide gas sealed instrument access to a body cavity, while maintaining a stable pressure within the body cavity (e.g., a stable pneumoperitoneum in the peritoneal or abdominal cavity). In contrast, the valve sealed access port 30 is a conventional or standard trocar, for providing access to a body cavity through a mechanical valve seal, such as, for example, a duckbill seal, septum seal or the like. Depending upon the requirements of a particular surgical procedure, the multi-modal gas delivery system 10 can be utilized with either the gas sealed access port 20, the valve sealed access port 30 or with both access ports 20, 30 at the same time.

The gas delivery system 10 further includes a compressor or positive pressure pump 40 for recirculating surgical gas through the gas sealed access port 20 by way of the gaseous sealing manifold 110. The compressor 40 is preferably driven by a brushless DC (direct-current) motor, which can be advantageously controlled to adjust gas pressure and flow rates within the gas delivery system 10, as disclosed for example in commonly assigned U.S. Pat. No. 10,702,306, which is incorporated herein by reference. Alternatively, the compressor 40 can be driven by an AC motor, but a DC motor will be relatively smaller and lighter, and therefore more advantageous from a manufacturing standpoint.

An intercooler and/or condenser 50 is operatively associated with the compressor 40 for cooling or otherwise conditioning gas recirculating through the gaseous sealing manifold 110. A UVC irradiator 52 is operatively associated with the intercooler or condenser 50 for sterilizing gas recirculating through the internal flow passages 54 formed therein by way of the compressor 40. In addition, the UVC irradiator 52 is intended to sterilize the interior surfaces of the gas conduits or flow passages 54 through which the gas flows within the intercooler/condenser 50.

The UVC irradiator preferably includes at least one LED light source or a florescent light source that is adapted and configured to generate UVC radiation at a wavelength of about between 240-350 nm, and preferably about 265 nm. This ultraviolet light at such a wavelength can sterilize viral, bacterial and microbial bodies within the gas conduits of the system, and can reduce coronavirus including SARS-COV-2.

Preferably, compressor 40, intercooler/condenser 50, gaseous sealing manifold 110 and insufflation manifold 210 are all enclosed within a common housing, which includes a graphical user interface and control electronics, as disclosed for example in commonly assigned U.S. Pat. No. 9,199,047, which is incorporated herein by reference.

The gas delivery system 10 further includes a surgical gas source 60 that communicates with the gaseous sealing manifold 110 and the insufflation manifold 210. The gas source 60 can be a local pressure vessel or a remote supply tank associated with a hospital or healthcare facility. Preferably, gas from the surgical gas source 60 flows through a high pressure regulator 65 and a gas heater 70 before it is delivered to the gaseous sealing manifold 110 and the insufflation manifold 210. Preferably, the high pressure regulator 65 and the gas heater 70 are also enclosed with the compressor 40, intercooler 50, gaseous sealing manifold 110 and insufflation manifold 210 in the common housing.

The gas delivery system 10 further includes a first outlet line valve (OLV1) 212 that is operatively associated with the insufflation manifold 210 for controlling a flow of insufflation gas to the valve sealed access port 30 and a second outlet line valve (OLV2) 214 that is operatively associated with the insufflation manifold 210 for controlling a flow of insufflation gas to the gas sealed access port 20.

In accordance with a preferred embodiment of the subject invention, the first and second outlet line valves 212, 214 of insufflation manifold 210 are proportional valves that are configured to dynamically alter or otherwise control the outflow of insufflation gas to the access ports 20, 30 to match volume fluctuations that may arise in a patient's body cavity as they occur. The first and second proportional outlet line valves 212, 214 provide the gas delivery system 10 with fine control of insufflation gas flow rate to achieve stable flow rates at lower pressure, reduce pressure oscillation and eliminate pneumatic hammer.

Because the first and second proportional outlet line valves 212, 214 are proximal to the patient where flow friction losses are relatively low, the gas delivery system 10 is able to measure peritoneal pressures accurately. Moreover, the use of proportional outlet line valves for this purpose is uniquely possible here, because there is constant gas recirculation throughout the gas delivery system 10, either by way of closed loop smoke evacuation or by way of the gas sealed access port 20.

Proportional valves allow for infinitely variable gas flow adjustment between a minimum flow state and a maximum flow state. Given that some volume changes in a patient's body cavity, such as breathing, are expected and consistent, by employing proportional outlet line valves, the insufflation manifold 210 is able to dynamically alter the gas flow to the body cavity to inverse the expected volume changes, resulting in a neutral effect on the pressure inside the cavity.

An additional benefit of using proportional valves for controlling the outflow of insufflation gas from manifold 210 is a reduction in response time, as compared to that of a solenoid valve. A solenoid valve operates by applying energy to coils, which produces an electromagnetic force that moves a piston. However, the energizing of the coils takes some amount of time, introducing a delay between a commanded action and the physical movement of the piston. In contrast, proportional valves, as employed in the gas delivery system 10 of the subject invention, do not have an energization delay in general, and so they have an improved response time as compared to solenoid valves.

The insufflation manifold 210 further includes a first patient pressure sensor (PWS1) 222 downstream from the first outlet line valve 212 and a second patient pressure sensor (PWS1) 224 downstream from the second outlet line valve 214. These two patient pressure sensors are used to measure abdominal pressure to control outlet line valves 212, 214, respectively. Two other pressure sensors are located upstream from the outlet line valves 212, 214, and are labeled as DPS1 and DPS2. These two pressure sensors are situated within a venturi to measure a pressure differential that is used to infer a total gas flow rate from the insufflation manifold 210 to the patient's body cavity.

A primary proportional valve (PRV) 216 is also operatively associated with insufflation manifold 210 and it is located upstream from the first and second outlet line valves 212, 214 to control the flow of insufflation gas to the first and second outlet line valves 212, 214. Proportional valve 216 functions to maintain an intermediate pressure within the insufflation manifold 210 (as the central node in the LPU) at a constant pressure between 1 and 80 mmHg, dependent on the system operating mode. The opening of PRV 216 can be indirectly initiated by any of the following actions: patient respiration, gas leakage downstream of PRV 216, or the opening of the safety valve LSV 227 or ventilation valve VEV 228, i.e. any event that causes an intermediate pressure to drop. In the system. LSV 227 and VEV 228 are described in more detail below.

The gaseous sealing manifold 110 also includes a high pressure gas fill valve (GFV) 112 that is operatively associated with an outlet side of the compressor 40. GFV 112 is adapted and configured to control gas delivered into the gaseous sealing manifold 110 from the source of surgical gas 60. Preferably, the gas fill valve 112 is a proportional valve that is able to dynamically control surgical gas delivered into the gaseous sealing manifold 110.

The gaseous sealing manifold 110 also includes a smoke evacuation valve (SEV) 114 that is operatively associated with an outlet side of the compressor 40 for dynamically controlling gas flow between the gaseous sealing manifold 110 and the insufflation manifold 210 under certain operating conditions, such as, for example, when the gas delivery device 10 is operating in a smoke evacuation mode. Preferably, the smoke evacuation valve 114 is a proportional valve.

A bypass valve (SPV) 116 is positioned between an outlet side of the compressor 40 and an inlet side of the compressor 40 for controlling gas flow within the gaseous sealing manifold 110 under certain operating conditions. Preferably, the bypass valve 116 is a proportional valve, which is variably opened to establish and control the gaseous seal generated within gas sealed access port 20. Moreover, bypass valve 116 controls gas flow rate to the gaseous seal using feedback from pressure sensors 122, 124, described in further detail below.

The gaseous sealing manifold 110 also includes an air ventilation valve (AVV) 118, which is operatively associated with an inlet side of the compressor 40 for controlling the entrainment of atmospheric air into the system 10 under certain operating conditions. For example, AVV 118 will permit the introduction of atmospheric air into the gaseous sealing circuit to increase the air mass (i.e., the standard volume) within the circuit. The thermodynamics of clinical use conditions can cause a loss of standard volume within the gas circuit. The ventilation valve 118 permits the gas delivery system 10 to make up for this lost volume, in order to ensure that pump pressure and flow rates are sufficient to maintain the gaseous seal within the gas sealed access port 20. The ventilation valve 118 can also be opened to reduce the vacuum side pressure in the gas seal circuit.

An overpressure relief valve (ORV) 120 is operatively associated with an outlet side of the compressor 40 for controlling a release of gas from the system 10 to atmosphere under certain operating conditions. Preferably, the overpressure relief valve 120 is a proportional valve that is opened to reduce the positively pressurized side of the gas seal circuit, especially in the event of an emergency, such as a loss of power to the gas delivery system 10. The normally open configuration of relief valve 120 reduces the risk of over-pressurization of the patient cavity upon loss of power to that valve.

A first pressure sensor (RLS) 122 is operatively associated with an inlet side of the compressor 40 and a second pressure sensor (PLS) 124 is operatively associated with an outlet side of the compressor 40. These pressure sensors 122, 124 are situated to have unobstructed and minimally restricted commutation with the patient's abdominal cavity in order to continuously and accurately measure cavity pressure. The signals from these two pressure sensors 122, 124 are employed by a controller of the gas delivery system 10 to modulate the opening of the two outlet line valves 212 and 214, to control the patient cavity pressure.

In addition, the gaseous sealing manifold 110 includes a gas quality sensor 126 that is operatively associated with an outlet side of the compressor 40. The gas quality sensor monitors the level of oxygen in the recirculation circuit, which corresponds to a concentration of $CO_2$ in the body cavity of a patient, as disclosed in U.S. Pat. No. 9,199,047.

A first blocking valve (BV1) 132 is operatively associated with an outlet flow path of the gaseous sealing manifold 110 and a second blocking valve (BV2) 134 is operatively associated with an inlet flow path to the gaseous sealing manifold 110. The blocking valves 132, 134 are employed during a self-test prior to a surgical procedure, as disclosed in U.S. Pat. No. 9,199,047. It is envisioned that the first and second blocking valves 132, 134 could be are mechanically actuated or pneumatically actuated.

A first filter element 142 is positioned downstream from the first blocking valve 132 for filtering pressurized gas flowing from the compressor 40 to the gas sealed access port 20, and a second filter element 144 is positioned upstream from the second first blocking valve 134 for filtering gas returning to the compressor 40 from the gas sealed access port 20. Preferably, the filter elements 142, 144 are housed within a common filter cartridge, as disclosed for example in U.S. Pat. No. 9,199,047.

The first and second blocking valves 132, 134 communicate with a blocking valve pilot (BVP) 226 that is included within with the insufflation manifold 210. Preferably, the blocking valve pilot 226 is a solenoid valve. It is envisioned that BVP 226 could be fed from the compressor outlet as shown or from a gas source such of surgical gas or air. The insufflation manifold 110 further includes a pressure sensor (PMS) 225 located downstream from the primary proportional valve 216 and upstream from the outlet line valves 212, 214. The two outlet line valves are opened to introduce insufflation gas to the patient's body cavity by way of the access ports 20, 30. This introduction of gas has the effect of increasing pressure within the body cavity. Additionally, the outlet line valves 212, 214 can be opened in conjunction with air ventilation valve 228 to release gas from the body cavity, having the effect of desufflation and reduction of cavity pressure.

The insufflation manifold 210 further includes a low pressure safety valve (LSV) 227 downstream from the primary proportional valve 216 and upstream from the first and second outlet line valves 212, 214 for controlling a release of gas from the system 10 to atmosphere under certain operating conditions. LSV 227 is a purely mechanical valve that functions to limit the maximum intermediate pressure within the manifold 210 or LPU (Low Pressure Unit) in the event of a power interruption, a pressure controller malfunction or if a valve located upstream from the LSV sticks in an open position.

In addition, a ventilation exhaust valve (VEV) 228 is positioned downstream from the primary proportional valve 216 and upstream from the outlet line valves 212, 214 for controlling a release of gas from the system 10 to atmosphere under certain operating conditions. The ventilation exhaust valve 228 is a preferably a proportional valve that is opened to de-sufflate or otherwise reduce patient cavity pressure. Additionally, VEV 228 can be opened to reduce intermediate pressure within the LPU.

A filter element 242 is positioned downstream from the first outlet line valve 212 for filtering insufflation gas flowing from the insufflation manifold 210 to the valve sealed access port 30. Another filter element 244 is positioned downstream from the second outlet line valve 224 for filtering insulation gas flowing from the insufflation manifold 210 to the gas sealed access port 20. Preferably, filter element 244 is housed with filter elements 142 and 144 in a common filter cartridge, while filter element 242 is separately located.

Figure 2:
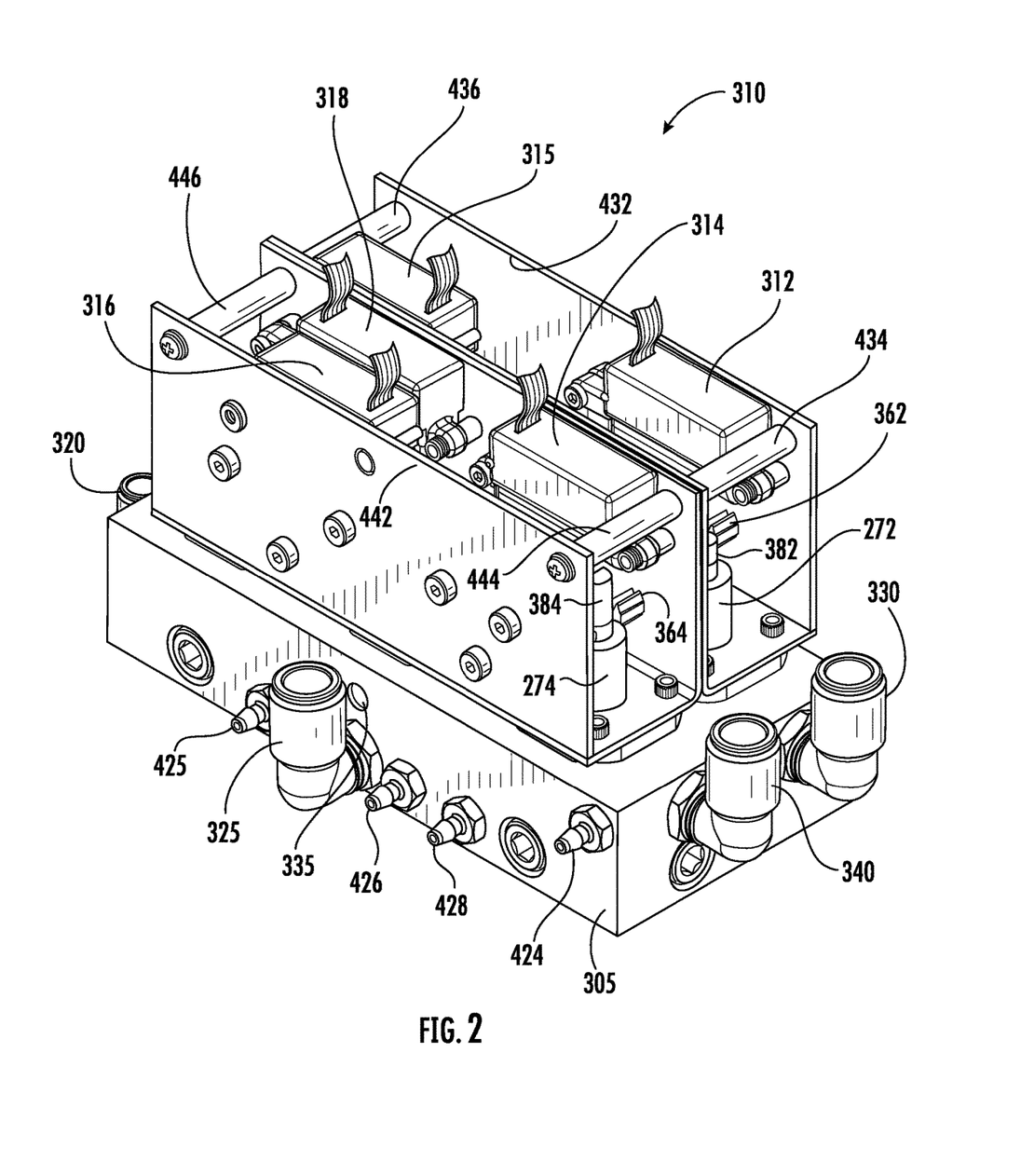
FIG. 2 is a perspective view of the insufflation manifold assembly for use in the gas delivery system shown in FIG. 1, which includes a plurality of motorized linear valve actuators.
Figure 3:
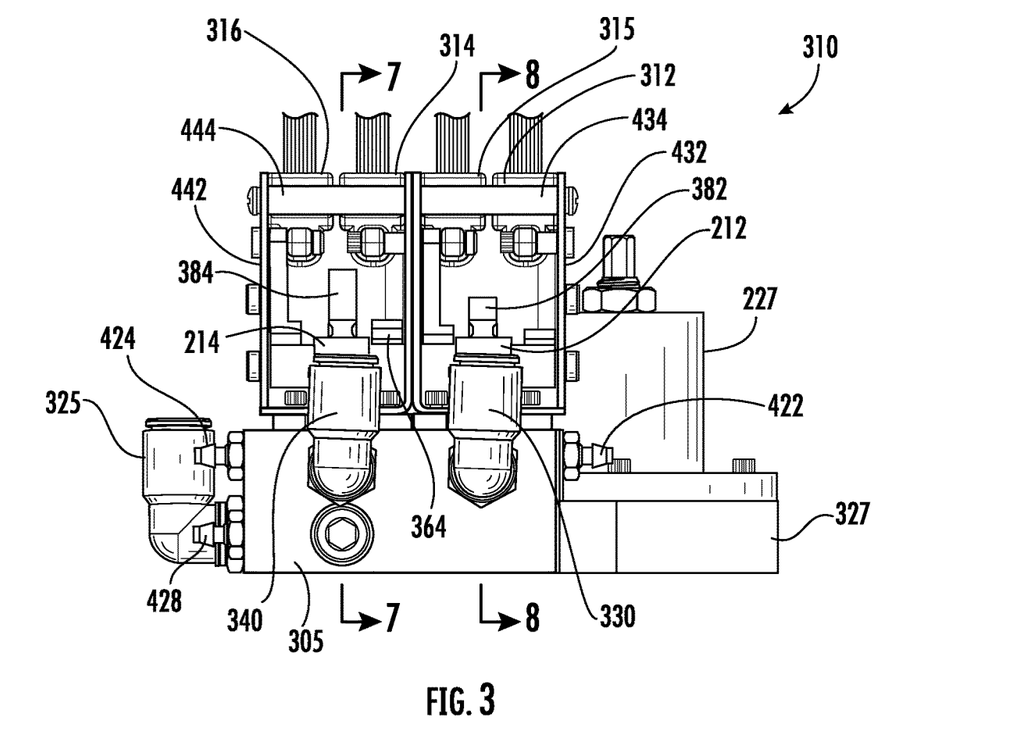
FIG. 3 is a right side elevational view of the insufflation manifold assembly shown in FIG. 2.
Figure 4:
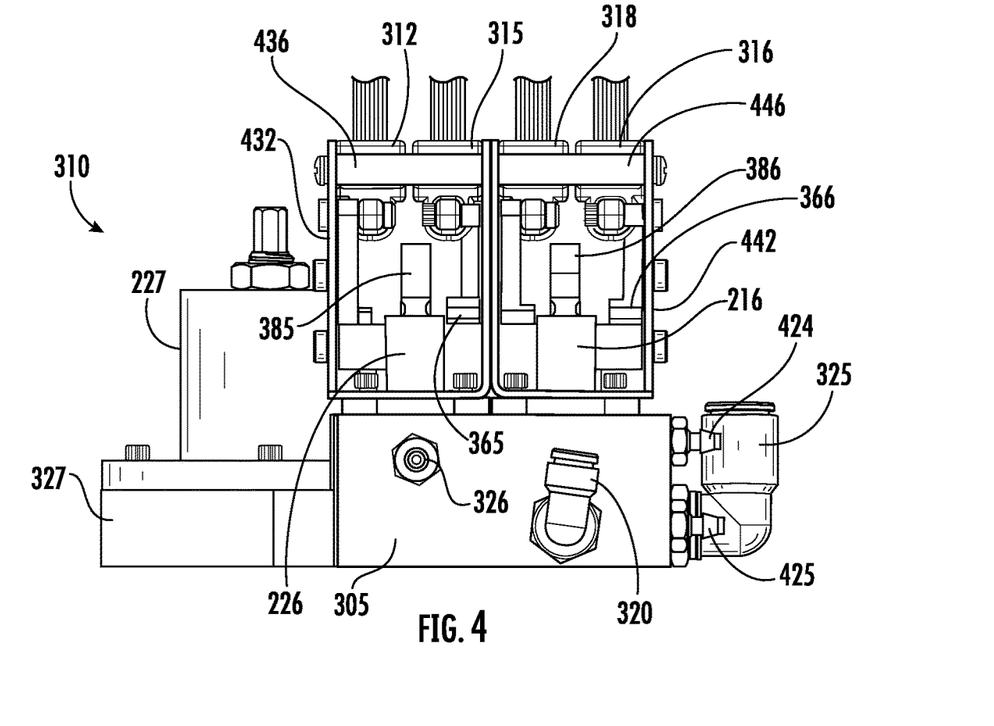
FIG. 4 is a left side elevational view of the insufflation manifold assembly shown in FIG. 2.
Figure 5:
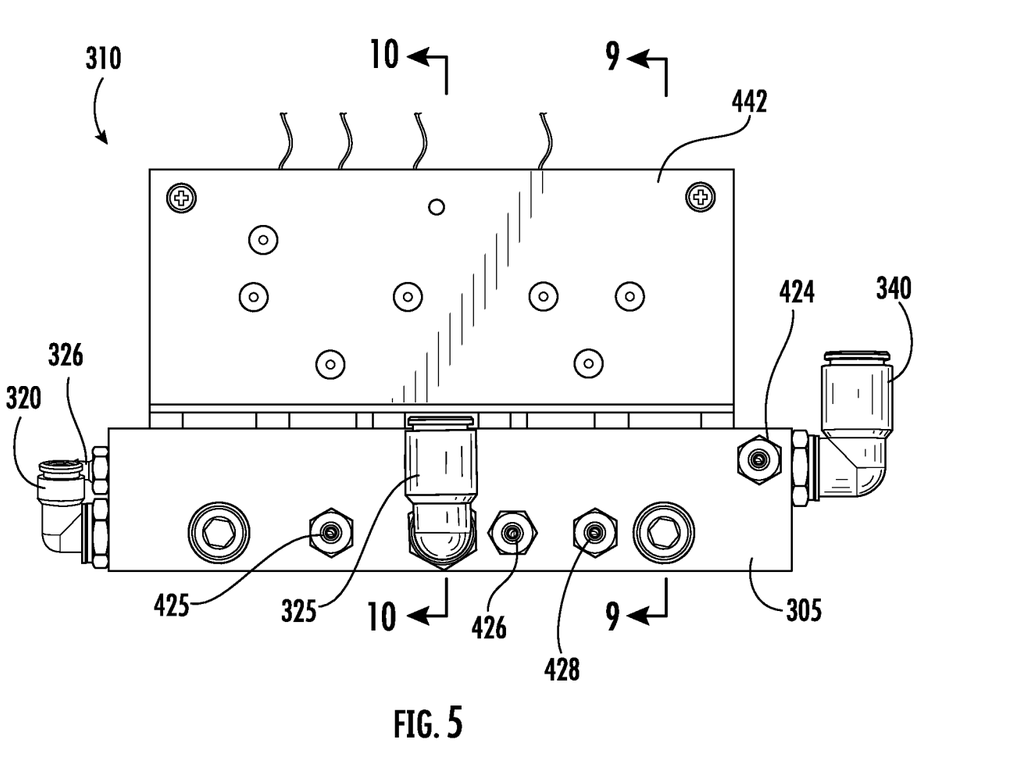
FIG. 5 is a front elevational view of the insufflation manifold assembly shown in FIG. 2.
Figure 6:
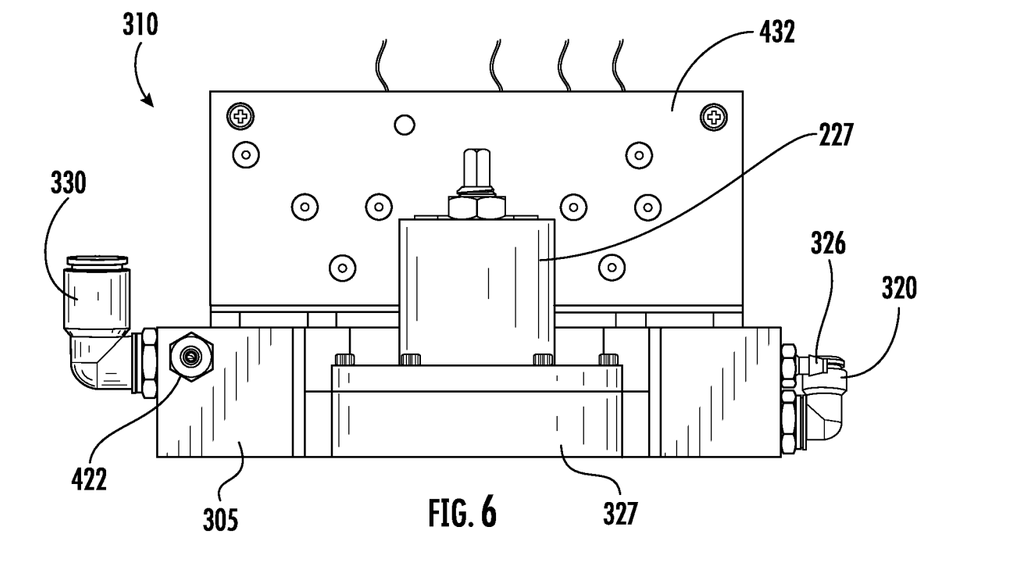
FIG. 6 is a rear elevational view of the insufflation manifold assembly shown in FIG. 2.
Figure 7:
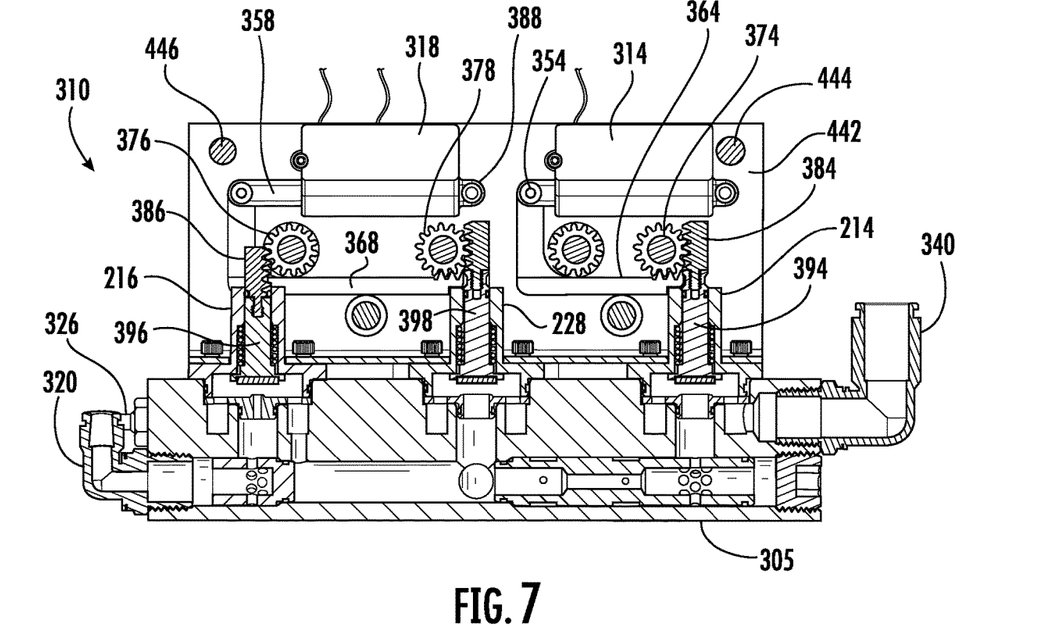
FIG. 7 is a cross-sectional view taken along line 7-7 of FIG. 3.

Referring now to FIG. 2, there is illustrated a low pressure insufflation manifold assembly constructed in accordance with a preferred embodiment of the subject invention and designated generally by reference numeral 310 which is adapted and configured for use in the gas delivery system 10 illustrated in FIG. 1. The insufflation manifold assembly 310 is designed as a compact, readily serviceable and replaceable modular unit. It includes a manifold body 305 having an inlet port 320 for receiving insufflation gas (i.e., $CO_2$ at 2.2 bar) from a gas source 60 by way of a high pressure regulator 65, as shown in FIG. 1.

The manifold body 305 also includes a first outlet port 330 for delivering insufflation gas to a first access port (i.e., the valve sealed access port 30 by way of filter element 242 as shown in FIG. 1) and a second outlet port 340 for delivering insufflation gas to a second access port (i.e., the gas sealed access port 20 by way of filter element 244 as shown in FIG. 1).

As shown in FIGS. 2 through 6, the manifold body 305 also includes an inlet port 325 for receiving pressurized gas (i.e., compressor discharge) from the gas sealed manifold 110 shown in FIG. 1, by way of the smoke evacuation valve (SEV) 114, under certain operating conditions. The location of the inlet port 325 can be moved to a different positon on the manifold body 305, for example, a plugged port location downstream from DPS1, DPS2.

Figure 10:
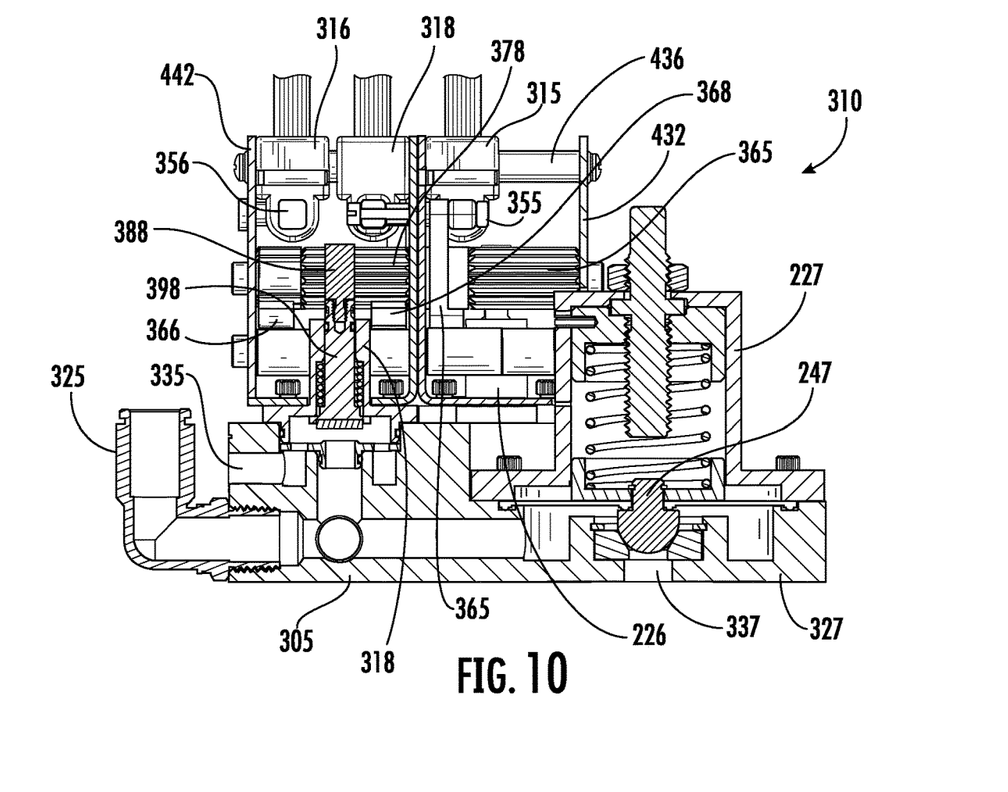
FIG. 10 is a cross-sectional view taken along line 10-10 of FIG. 5.

The manifold body 305 further includes a first exhaust/vent port 335 venting to atmosphere, which communicates with the ventilation valve (VEV) 228 (see FIGS. 2 and 10), and a second exhaust/vent port 337 venting to atmosphere, which communicates with the low pressure safety valve (LSV) 227 (see FIG. 10). As best seen in FIG. 10, the low pressure safety valve 227 is a mechanical valve for controlling the release of gas from the safety exhaust/vent port 337 to limit a maximum intermediate pressure within the manifold assembly in the event of a power interruption, a pressure controller malfunction or if another valve sticks in an open position. The mechanical safety valve 227 includes a spring biased valve member 247 that will open when intermediate pressure exceeds a manually adjustable preset pressure. This will limit patient pressure to no more that the preset pressure in the event upon a control malfunction or loss of power. In such an instance, gas will be released through the lower vent port 337 formed in the support base 337 of safety valve 227.

Manifold body 305 also includes a port 337 facilitating communication between the blocking valve pilot valve 226 and the blocking valves 132 (BV1), 134 (BV2) remote from the insufflation manifold assembly 310. The manifold body 305 further includes sensor ports 422, 424 that communicate with patient pressure sensors 222 (PWS1) and 224 (PWS2), respectively. In addition, the manifold body 305 includes sensor ports 426,428 that communicate with the pressure differential sensors DPS1 and DPS2. Another sensor port 425 is provided on manifold body 305 for communicating with the intermediate pressure sensor 225 (PMS) located downstream from the primary proportional valve 216 (PRV).

Figure 8:
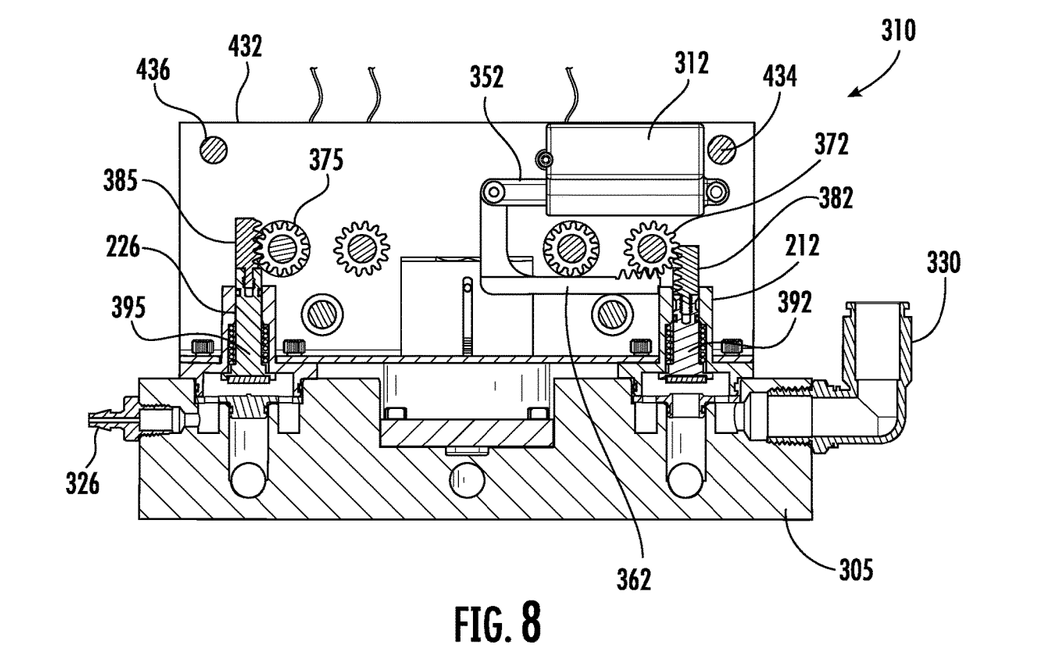
FIG. 8 is a cross-sectional view taken along line 8-8 of FIG. 3.
Figure 9:
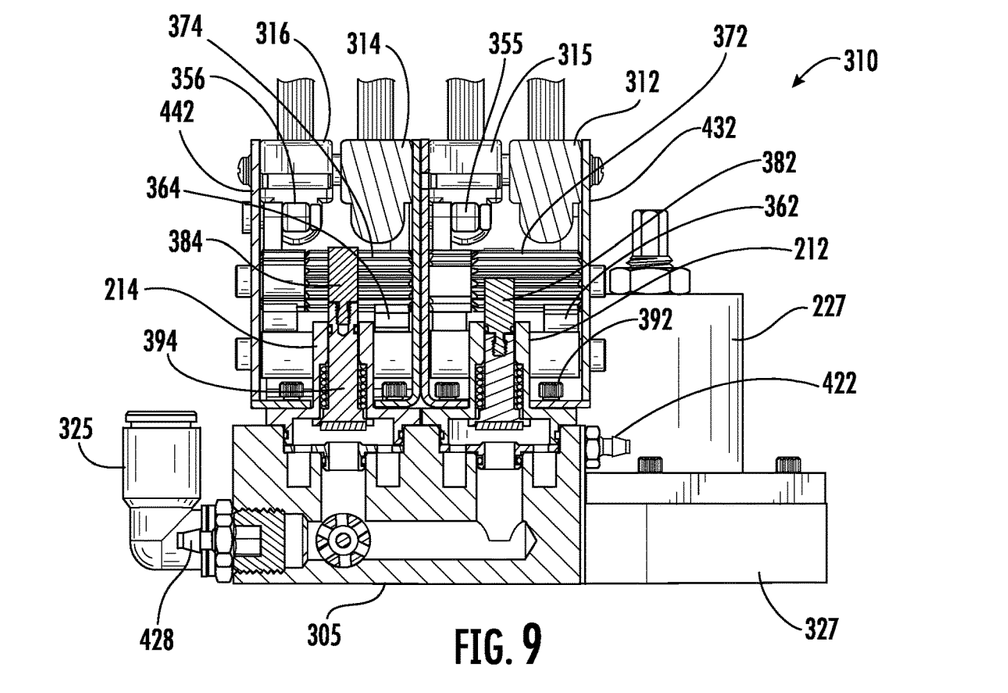
FIG. 9 is a cross-sectional view taken along line 9-9 of FIG. 5.

As best seen in FIGS. 8 through 10, the manifold body 305 defines a series of interconnected internal drilled passageways that facilitate the flow of insufflation gas and air between and among the various control valves and sensors of the insufflation manifold assembly 310. Those skilled in the art will readily appreciate that the arrangement and location of these passageways within the manifold body 305 could vary by design and therefore should not be considered as a limitation on the scope of the subject invention.

Referring now to FIGS. 7 through 10, each motorized linear actuator (312, 314, 315, 316, 318) includes a respective rack and pinion mechanism to effectuate precise dynamic control of a respective valve. Each rack and pinion mechanism includes a respective horizontal actuation shaft (352, 354, 355, 356, 358) and a respective corresponding horizontal drive rack gear (362, 364, 365, 366, 368). In addition, each motorized linear actuator (312, 314, 315, 316, 318) includes a rotatable drive pinion gear (372, 374, 375, 376, 378) that is driven by the horizontal drive rack gear (362, 364, 365, 366, 368), and a vertical driven rack gear (382, 384, 385, 386, 388) that is driven by the driven pinon gear (372, 374, 375, 376, 378) and operatively associated with a spring-loaded vertical valve stem (392, 394, 395, 396, 398). Each horizontal drive rack gear (362, 364, 365, 366, 368) is mounted to translate along a first horizontal axis, and each rotatable driven pinion gear (372, 374, 375, 376, 378) is mounted to rotate about a second horizontal axis that extends perpendicular to the first horizontal axis.

In use, upon receiving a command from a controller of gas delivery system 10, linear movement of a horizontal actuation shaft (right or left) will cause corresponding liner movement of an associated horizontal gear rack (right or left), which will rotate a corresponding pinion gear (clockwise or counter-clockwise). That pinon gear will then move an associated vertical drive rack (up or down), which in turn will control the upward or downward movement of a corresponding valve stem (392, 394, 395, 396, 398) of a control valve (212 (OLV1), 214 (OLV2), 226 (BVP), 216 (PRV), 228 (VEV)).

The five motorized linear actuators (312, 314, 315, 316 and 318) are arranged in two side-by-side groups on manifold body 305. More particularly, the linear actuator 312 of the OLV1 valve 212 and the linear actuator 315 of the BVP valve 226 are grouped together within a first housing 432. And, the linear actuator 314 of the OLV2 valve 214, the linear actuator 316 of the PRV valve 216 and the linear actuator 318 of the VEV valve 228 are ganged together within a second housing 442.

Front and rear upper transverse spacer rods 434 and 436 provide structural rigidity to the first housing 432, while front and rear upper transverse spacer rods 444 and 446 provide structural rigidity to the second housing 442. Those skilled in the art will appreciate from the figures that the flat ribbon cables associated with each of the linear actuators (312, 314, 315, 316 and 318) extend to a controller of the gas delivery system 10 which delivers power and control signals to the five motorized actuators.

Figure 11:
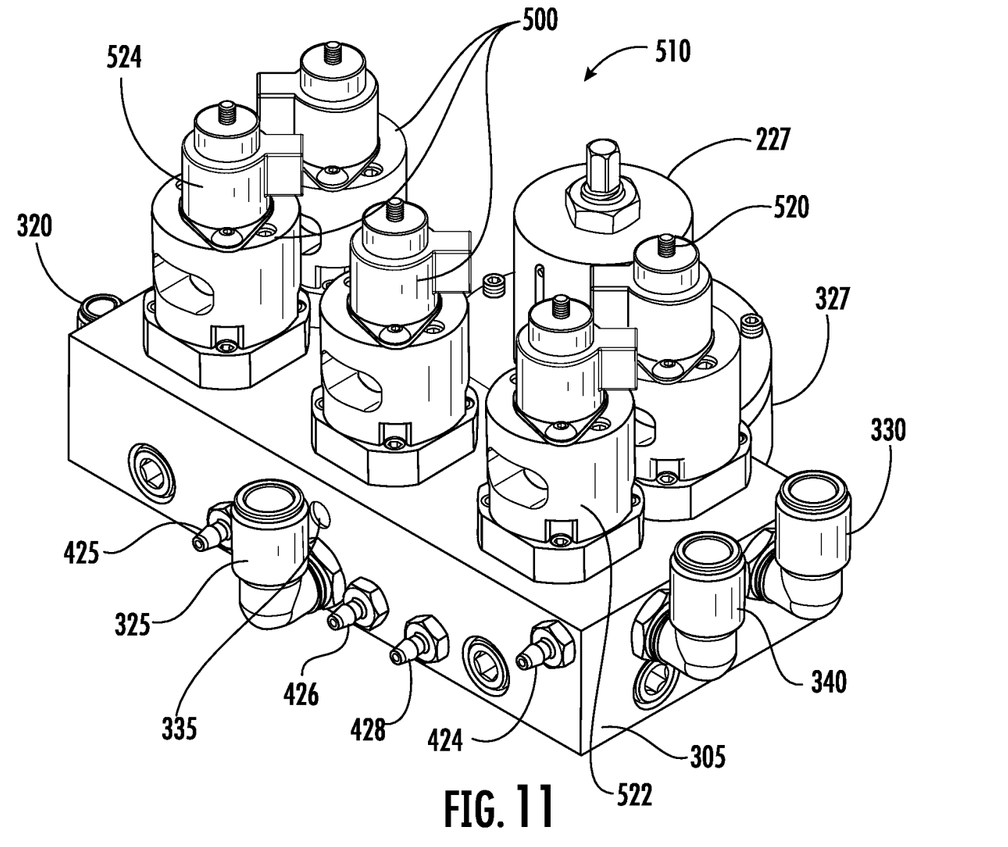
FIG. 11 is a perspective view of another insufflation manifold assembly for use in the gas delivery system of FIG. 1, which includes a plurality of motorized rotary valve actuators.

Referring now to FIG. 11, there illustrated another low pressure insufflation manifold assembly constructed in accordance with a preferred embodiment of the subject invention and designated generally by reference numeral 510 which is adapted and configured for use in the gas delivery system 10 illustrated in FIG. 1. Manifold assembly 510 is substantially similar to manifold assembly 310 shown in FIG. 2, in that it includes the same proportional control valves for dynamically controlling gas flow (i.e., OLV1, OLV2, BVP, PRV, VEV), but in this embodiment of the subject invention, these proportional control valves have respective motorized rotary actuators 500, rather the than motorized linear actuators (312, 314, 315, 316, 318) described above.

Figure 12:
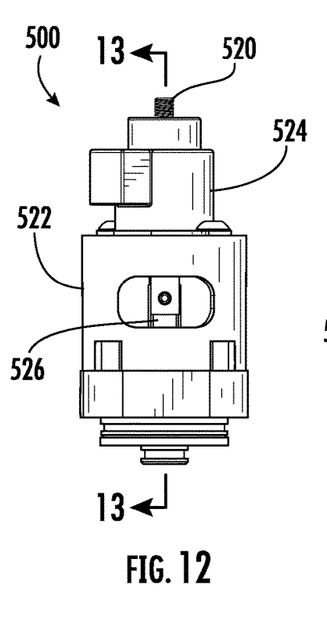
FIG. 12 is an elevational view of the rotary actuator.
Figure 13:
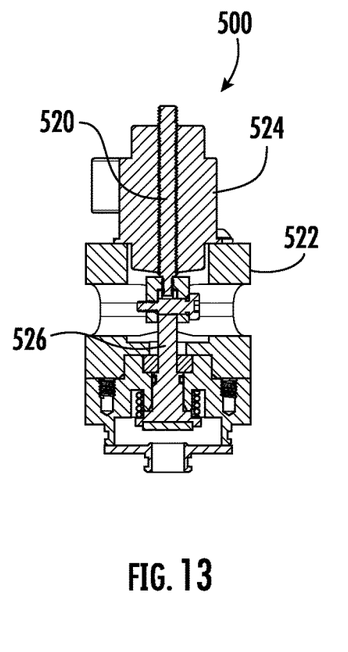
FIG. 13 is a cross-sectional view of the rotary actuator taken along line 13-13 of FIG. 12.
Figure 14:
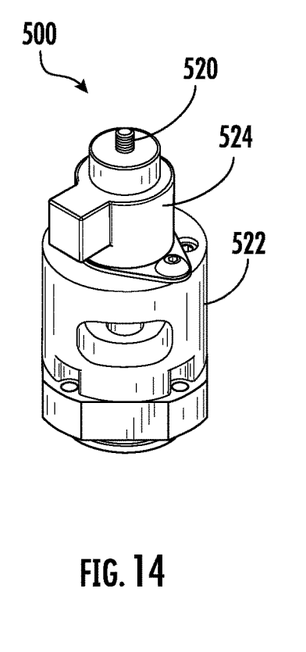
FIG. 14 is a perspective view of the rotary actuator.

More particularly, as shown in FIGS. 12 through 14, each motorized rotary actuator 500 includes an axial drive screw 520 that is supported for vertical translation within a housing 522 driven by a DC rotary stepper motor 524. In each rotary actuator, the axial drive screw 520 is operatively associated with a spring-loaded vertical valve stem 526 associated with a respective one of the five control valves 212, 214, 226, 216, 228 depicted in FIG. 1. In use, rotation of the drive screw 520 causes corresponding vertical movement of the valve stem 526 to dynamically adjust the amount of gas flowing through the associated control valve.

Figure 15:
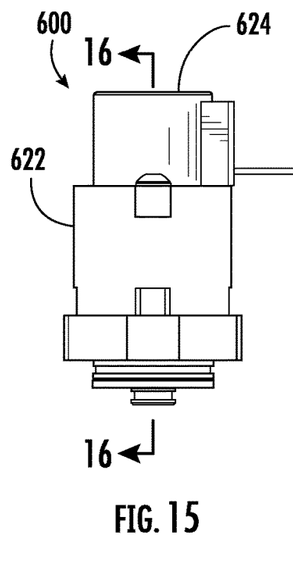
FIG. 15 is an elevational view of the rotary actuator.
Figure 16:
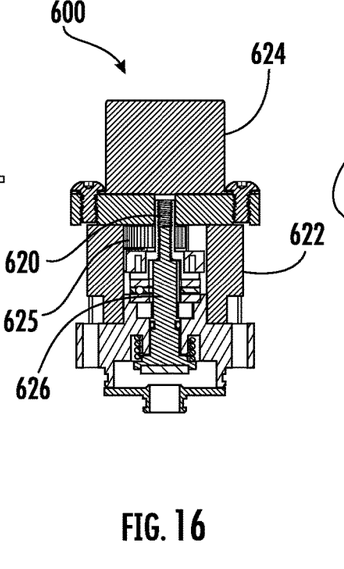
FIG. 16 is a cross-sectional view of the rotary actuator taken along line 16-16 of FIG. 15.
Figure 17:
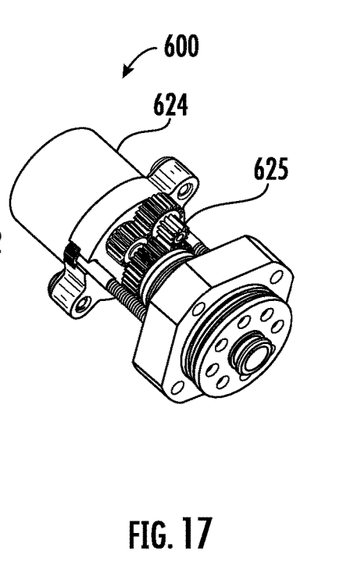
FIG. 17 is a perspective view of the rotary actuator.

Alternatively, as shown in FIGS. 15 through 17 a motorized rotary actuator 600 may be employed in gaseous sealing manifold assembly 510 for dynamically controlling gas flow, each of which includes a reduction gear assembly 625 that is supported within a housing 622 driven by a DC rotary stepper motor 624. The reduction gear assembly reduces the torque generated by the stepper motor. In each rotary actuator, the reduction gear assembly 625 is operatively associated with a drive screw 620 and a spring-loaded vertical valve stem 626 connected thereto. In use, actuation of the reduction gear assembly causes corresponding vertical movement of the drive screw 620 and attached valve stem 626 to dynamically adjust the amount of gas flowing through the associated control valve (i.e., 212, 214, 226, 216, 228).

While the gas delivery system of the subject disclosure has been shown and described with reference to preferred embodiments, those skilled in the art will readily appreciate that changes and/or modifications may be made thereto without departing from the scope of the subject disclosure.

What is claimed is:

1. A manifold assembly for a surgical gas delivery system comprising:
    a) a three-dimensional manifold body having a horizontal top surface and a plurality of vertical side surfaces including a first side surface and a second side surface, and including an inlet port for receiving insufflation gas from a gas source by way of a high pressure regulator, a first outlet port for delivering the insufflation gas to a first access port and a second outlet port for delivering the insufflation gas to a second access port, wherein the inlet port is located on the first side surface of the manifold body, and the first outlet port and the second outlet port are located on the second side surface of the manifold body;
    b) a first outlet line valve located on the top surface of the manifold body and communicating with the first outlet port through internal passageways defined within the manifold body, wherein the first outlet line valve includes an electro-mechanical valve actuator for dynamically controlling a flow of the insufflation gas to the first access port;
    c) a second outlet line valve located on the top surface of the manifold body and communicating with the second outlet port through the internal passageways defined within the manifold body, wherein the second outlet line valve includes an electro-mechanical valve actuator for dynamically controlling the flow of the insufflation gas to the second access port; and
    d) a primary proportional valve located on the top surface of the manifold body and communicating with the first outlet line valve and the second outlet line valve through the internal passageways defined within the manifold body for maintaining a constant pressure within the manifold body upstream from the first outlet line valve and the second outlet line valve.

2. The manifold assembly recited in claim 1, wherein the manifold body further includes an exhaust port for venting a gas to an atmosphere, wherein a ventilation exhaust valve is operatively associated with the exhaust port, and wherein the ventilation exhaust valve includes an electro-mechanical valve actuator for dynamically controlling the venting of the gas from the exhaust port.

3. The manifold assembly recited in claim 2, wherein the manifold body further includes a safety vent port for releasing the gas to the atmosphere, and a low pressure safety valve is operatively associated with the safety vent port, and wherein the low pressure safety valve is a mechanical valve for controlling the release of the gas from the safety vent port to limit a maximum intermediate pressure within the manifold assembly in an event of a power interruption, a pressure controller malfunction, or if another valve sticks in an open position.

4. The manifold assembly recited in claim 3, wherein the primary proportional valve includes an electro-mechanical valve actuator for dynamically controlling a flow of the insufflation gas to the first outlet line valve and the second outlet line valve.

5. The manifold assembly recited in claim 4, wherein the manifold body includes a communication port for communicating with a pair of blocking valves remote from the manifold assembly, wherein a blocking valve pilot valve is operatively associated with the communication port located upstream from the primary proportional valve, and wherein the blocking valve pilot valve includes an electro-mechanical valve actuator for dynamically controlling a flow of the gas therethrough.

6. The manifold assembly recited in claim 4, wherein the manifold body includes a pressure sensor port downstream from the primary proportional valve and upstream from the first outlet line valve and the second outlet line valve.

7. The manifold assembly recited in claim 1, wherein the electro-mechanical valve actuator of the first outlet line valve and the electro-mechanical valve actuator of the second outlet line valve are each a motorized rotary actuator, which each include an axial drive screw operatively associated with a vertical valve stem.

8. The manifold assembly recited in claim 1, wherein the manifold body includes a first patient pressure sensor port downstream from the first outlet line valve and a second patient pressure sensor port downstream from the second outlet line valve for measuring abdominal pressure.

9. The manifold assembly recited in claim 1, wherein the manifold body includes a first pressure sensor port and a second pressure sensor port upstream from the first outlet line valve and the second outlet line valve to measure a pressure differential used to infer a total gas flow rate from the manifold body to a body cavity of a patient.

10. The manifold assembly recited in claim 1, wherein the first access port is a valve sealed access port and the second access port is a gas sealed access port.

11. A manifold assembly for a surgical gas delivery system comprising:
    a) a three-dimensional manifold body having a horizontal top surface and a plurality of vertical side surfaces including a first side surface and a second side surface, and including an inlet port for receiving insufflation gas from a gas source by way of a high pressure regulator, a first outlet port for delivering the insufflation gas to a valve sealed access port and a second outlet port for delivering the insufflation gas to a gas sealed access port, wherein the inlet port is located on the first side surface of the manifold body, and the first outlet port and the second outlet port are located on the second side surface of the manifold body;

b) a first outlet line valve located on the top surface of the manifold body and communicating with the first outlet port through internal passageways defined within the manifold body, wherein the first outlet line valve includes a motorized rotary valve actuator for dynamically controlling a flow of the insufflation gas to the valve sealed access port;

c) a second outlet line valve located on the top surface of the manifold body and communicating with the second outlet port through the internal passageways defined within the manifold body, wherein the second outlet line valve includes a motorized rotary valve actuator for dynamically controlling the flow of the insufflation gas to the gas sealed access port; and d) a primary proportional valve located on the top surface of the manifold body and communicating with the first outlet line valve and the second outlet line valve through the internal passageways defined within the manifold body for maintaining a constant pressure within the manifold body upstream from the first outlet line valve and the second outlet line valve.

12. The manifold assembly recited in claim 11, wherein the manifold body further includes an exhaust port for venting a gas to an atmosphere, wherein a ventilation exhaust valve is operatively associated with the exhaust port, and wherein the ventilation exhaust valve includes a motorized rotary valve actuator for dynamically controlling the venting of the gas from the exhaust port.

13. The manifold assembly recited in claim 12, wherein the manifold body further includes a safety vent port for releasing the gas to the atmosphere, and a low pressure safety valve is operatively associated with the safety vent port, and wherein the low pressure safety valve is a mechanical valve for controlling the release of gas from the safety vent port to limit a maximum intermediate pressure within the manifold assembly in an event of a power interruption, a pressure controller malfunction, or if another valve sticks in an open position.

14. The manifold assembly recited in claim 13, wherein the primary proportional valve includes a motorized rotary valve actuator for dynamically controlling a flow of the insufflation gas to the first outlet line valve and the second outlet line valve.

15. The manifold assembly recited in claim 14, wherein the manifold body includes a communication port for communicating with a pair of blocking valves remote from the manifold assembly, wherein a blocking valve pilot valve is operatively associated with the communication port located upstream from the primary proportional valve, and wherein the blocking valve pilot valve includes a motorized rotary valve actuator for dynamically controlling a flow of the gas therethrough.

16. The manifold assembly recited in claim 15, wherein the motorized rotary valve actuator of the first outlet line valve, the motorized rotary valve actuator of the second outlet line valve, the motorized rotary valve actuator of the primary proportional valve, and the motorized rotary valve actuator of the blocking valve pilot valve includes a reduction gear assembly operatively associated with a vertical valve stem.

17. The manifold assembly recited in claim 15, wherein the motorized rotary valve actuator of the first outlet line valve, the motorized rotary valve actuator of the second outlet line valve, the motorized rotary valve actuator of the primary proportional valve, and the motorized rotary valve actuator of the blocking valve pilot valve includes an axial drive screw operatively associated with a vertical valve stem.

18. A manifold assembly for a surgical gas delivery system comprising:

a) a three-dimensional manifold body having a horizontal top surface and vertical side surfaces including a first side surface and a second side surface, and including an inlet port on the first side surface of the manifold body for receiving insufflation gas, and at least one outlet port on the second side surface of the manifold body for delivering the insufflation gas to an access port;

b) an outlet line valve located on the top surface of the manifold body and communicating with the at least one outlet port through internal passageways defined within the manifold body for controlling a flow of the insufflation gas to the access port; and c) a primary proportional valve located on the top surface of the manifold body and communicating with the outlet line valve through the internal passageways defined within the manifold body to dynamically control the flow of the insufflation gas to the outlet line valve.

19. The manifold assembly recited in claim 18, wherein the outlet line valve is a proportional valve having a motorized rotary valve actuator for dynamically controlling the flow of insufflation gas to the access port.

20. The manifold assembly recited in claim 18, wherein the primary proportional valve has a motorized rotary valve actuator.

* * * * *